(12) United States Patent
Bala et al.

(10) Patent No.: US 9,360,464 B2
(45) Date of Patent: Jun. 7, 2016

(54) DUAL MIGRATING INDICATOR

(71) Applicant: DANA PRODUCTS, INC., Franklin Park, IL (US)

(72) Inventors: Harry Bala, South Barrington, IL (US); Mark Bala, Chicago, IL (US)

(73) Assignee: American Sterilizer Company, Mentor, OH (US)

( * ) Notice: Subject to any disclaimer, the term of this patent is extended or adjusted under 35 U.S.C. 154(b) by 155 days.

(21) Appl. No.: 14/197,932

(22) Filed: Mar. 5, 2014

(65) Prior Publication Data

US 2015/0252403 A1    Sep. 10, 2015

(51) Int. Cl.
   *G01N 21/75* (2006.01)
   *G01N 31/22* (2006.01)
   *G01N 33/52* (2006.01)

(52) U.S. Cl.
   CPC .................... *G01N 31/226* (2013.01)

(58) Field of Classification Search
   CPC ....... G01N 31/226; G01N 33/525; A61L 2/28
   USPC ........................................ 422/420
   See application file for complete search history.

(56) References Cited

U.S. PATENT DOCUMENTS

| | | | |
|---|---|---|---|
| 3,313,266 A | 4/1967 | Kelson | |
| 3,341,238 A | 9/1967 | White | |
| 3,652,249 A | 3/1972 | White | |
| 3,981,683 A | 9/1976 | Larsson | |
| 4,410,493 A | 10/1983 | Joslyn | |
| 4,448,548 A * | 5/1984 | Foley | G01N 31/226 252/408.1 |
| 5,158,363 A * | 10/1992 | Speelman | A61L 2/28 116/207 |
| 5,378,430 A * | 1/1995 | Nieves | A61L 2/28 116/207 |
| 5,602,804 A * | 2/1997 | Haas | G01K 3/04 116/206 |
| 5,709,472 A | 1/1998 | Prusik | |
| 5,895,627 A | 4/1999 | Khachatoorian | |
| 7,718,125 B2 | 5/2010 | Bala | |
| 7,740,802 B2 | 6/2010 | Bala | |
| 7,790,105 B2 | 9/2010 | Bala | |
| 7,811,516 B2 | 10/2010 | Bala | |
| 2009/0047176 A1 * | 2/2009 | Cregger | A61L 2/28 422/28 |
| 2011/0275159 A1 * | 11/2011 | Landgrebe | A61L 2/28 436/1 |

FOREIGN PATENT DOCUMENTS

| | | |
|---|---|---|
| EP | 0022284 A1 | 1/1981 |
| WO | wo9524622 A1 * | 2/1995 |
| WO | 9524622 A1 | 9/1995 |

OTHER PUBLICATIONS

International Search Report for PCT/US2015/017090 dated Jun. 8, 2015.
International Search Report for PCT/US2013/068464 dated Feb. 21, 2014.

* cited by examiner

*Primary Examiner* — Jill Warden
*Assistant Examiner* — Brittany Fisher
(74) *Attorney, Agent, or Firm* — Levenfeld Pearlstein, LLC

(57) ABSTRACT

An indicator for a sterilization process is configured to function for two different sterilization conditions. The indicator includes two pass zones to indicate whether an acceptable sterilization has occurred after a sterilization process at a first condition of after a sterilization process at a second condition.

7 Claims, 1 Drawing Sheet

DUAL MIGRATING INDICATOR

BACKGROUND OF THE INVENTION

It is well known that heat destroys microorganisms. The presence of moisture accelerates this destruction by denaturing or coagulation of the proteins making up the microorganisms. Most microorganisms contain sufficient water so that moderate heat alone, e.g. 80° C.-100° C., will destroy the microorganism. Many bacterial spores, on the other hand, contain substantially no water and require elevated temperatures in excess of 150° C. for their destruction where dry heat is used. Hence, the destruction of such organisms is generally carried out in the presence of steam in autoclaves.

Such steam sterilization is generally carried out at temperatures of about 250° F. (121° C.) for at least 12 to 15 minutes or for shorter times at higher temperatures e.g. 270° F. (132° C.). Often, to ensure as sufficient safety margin, times as long as 30 minutes are used. Such long sterilization times give the operator a greater degree of confidence that steam has penetrated throughout the autoclave and among all of its contents. However, such long heat cycles are disadvantageous from the standpoint of economy of time, energy consumption, and severe shortening of the useful life of certain types of sterilized material, e.g., fabric gowns, drapes, and the like.

From time to time attempts have been made to develop sterilization indicators which permit quality control of sterilization with the confidence that all microorganisms have been destroyed. One presently used method is through the use of spore strips or samples. Spores which are particularly difficult to destroy are selected as the control standard, e.g., *Bacillus Subtilis* var. *Niger* and *Bacillus Stearothermophilus*. The spore strip or sample is placed in the autoclave with the materials to be sterilized. At the end of the sterilization cycle, the spore strip or sample is studied to determine whether it is possible to grow organisms in a suitable culture medium. Failure of the spores to reproduce indicates death of spores, and hence, adequate sterilization.

Although this control technique is accurate, it suffers from several inherent disadvantages; (1) excessive cost; (2) delay between processing and control data, (3) batch to batch variation of the spores, and (4) heat resistance of spores decreases with storage time.

Several attempts have been made to devise chemical type sterility indicators. One such product is known as Temp-Tube, and is disclosed in, for example, Kelson, U.S. Pat. No. 3,313,266 White, U.S. Pat. No. 3,341,238, and White, U.S. Pat. No. 3,652,249. The device consists of a sealed tube containing a compound with a melting point which corresponds to the sterilization temperature. The device is capable of indicating whether or not the autoclave was held at a temperature above or below the melting point for a period of time once the melting point is reached.

Other sterility indicators are known. One such indicator is disclosed in Larsson, U.S. Pat. No. 3,981,683, and uses a backing strip of aluminum foil having an organic compound containing oxygen or nitrogen in contact with a wicking strip, and a cover strip overlying the organic compound and the wicking strip. The cover strip is a polymeric rate controlling film that permits water vapor to pass through at a rate sufficient to make the strip operable at a temperature to be monitored.

One drawback to the device in Larsson is that the temperature and time parameters at which the indictor indicates an acceptable level of sterilization (e.g., that the temperature has been held at a minimum value for a specified period of time) is not well controlled. As such, the indicator can indicate that the requisite level of sterilization has occurred when in fact is has not.

Another such indicator is disclosed in Foley, U.S. Pat. No. 4,448,548. The device in Foley is directed to a steam sterilization indicator in which a fusible material, in tablet form, is deposited in an embossment in an aluminum backing. A wicking strip is attached to the backing in close proximity to the fusible tablet. A clear plastic material covers the tablet and the strip and is adhered to the backing.

The melting point of the fusible tablet, is depressed in the presence of saturated steam. Upon melt, the material in the tablet is absorbed by the wicking strip, producing a color front to provide an indication of the integration of time and temperature in the presence of steam. Various amounts of a binder are used in the tablet to provide a device which may be adjusted to reflect the thermal death curves of various types of microorganisms. The cover and the wick are bonded to the backing by an acrylic adhesive which also affects the rate of the indicator.

As with the Larsson device, a drawback to the device in Foley is that the temperature and time parameters at which the indictor indicates an acceptable level of sterilization is not well controlled and as such, the indicator can indicate that the requisite level of sterilization has occurred when in fact it has not.

Further, U.S. application Ser. Nos. 13/031,491 and 13/432,807, which are assigned to the Applicant of the present application and incorporated herein by reference, disclose sterilization test strips that, in a sense, mimic spore kill. These test strips are configured to indicate whether an acceptable level of sterilization has occurred after a predetermined time at a predetermined temperature. For example, a test strip can be configured to indicate whether an acceptable level of sterilization has occurred after 4 minutes at 134° C. However, these test strips are configured to work for one specific sterilization condition (e.g. 4 minutes at 134° C. Thus, a different test strip is required for each different sterilization condition. For example, the test strip configured to work for the 4 minutes at 134° C. sterilization condition will not work for the 12 minutes at 121° C. sterilization condition, and thus, the latter sterilization condition requires a different test strip. As such, users who perform sterilization processes in multiple different conditions are forced to purchase and stock multiple different test strips, which can increase operation costs and lead to user errors in selecting a correct indicator.

Test strips for two different sterilization conditions have also been introduced. However, these test strips are configured with two different indicator chemicals for each sterilization condition. Thus, these test strips are essentially two test strips put together into one test strip, and thus, they are bulkier and costly.

Therefore, there is a need for an improved sterility indicator that can be used for multiple sterilization conditions.

BRIEF SUMMARY OF THE INVENTION

A dual indicator for a sterilization process is configured to work for two different sterilization conditions. The dual indicator includes two pass zones, each of which is configured to indicate whether an acceptable sterilization has occurred after a different sterilization condition. As such, the dual indicator can replace two different Class 6 sterilization indicators, and thus, can reduce, the number of different test indicators required for users.

In one aspect, a dual indicator for two different sterilization conditions is provided. The dual indicator includes a base element, a first adhesive layer, an indicator chemical composition, a wicking material, a film layer, a second adhesive layer, a paper layer, and first and second pass zones. The base element is formed from a thermally conductive material having a length and a width. The base element has a recess formed therein extending along about a longitudinal centerline thereof, in which the recess is formed within the base material less than the length and the width of the base material. The first adhesive layer is disposed on the base element, and an indicator chemical composition deposited in the recess.

The wicking material is positioned at least in part in contact with the indicator chemical composition and positioned at least in part within the recess. The wicking material extends less than the length and width of the base element. The film layer is positioned over the base element, the wicking material and the indicator chemical composition. Further, the paper layer is disposed over the film layer, and a second adhesive layer is disposed between the paper layer and the film layer. The paper layer and the second adhesive layer include a window therein. The dual indicator also includes a first pass zone and a second pass zone, which are configured to indicate whether an acceptable level of sterilization has occurred for two different sterilization conditions.

The dual indicator is configured to indicate that an acceptable level of sterilization has occurred when the indicator chemical composition wicks along the wicking material to a location within the first pass zone after as sterilization process at a first predetermined temperature for a first, predetermined period of time, or when the indicator chemical composition wicks along the wicking material to a location within the second pass zone after a sterilization process at a second predetermined temperature for a second predetermined period of time.

In one embodiment, the indicator chemical composition contains a temperature sensitive material. Further, the indicator chemical composition may contain a dye. For example, the indicator chemical composition can contain a temperature sensitive material and a dye in a concentration of about 0.01 percent by weight of the indicator chemical composition.

Further, the film may be turned from a cast polypropylene, such as a cast polypropylene having a thickness of about 20 to 2.2 mils or a thickness of about 3.0 to 3.2 mils. The base element may be formed from aluminum having a thickness of about 3 mils.

In some embodiments, the first adhesive layer is formed from an acrylic adhesive, and the second adhesive layer may also be formed from an acrylic adhesive.

Further, the paper layer may include a first marker and a second marker, in which the first maker is longitudinally spaced from the indicator chemical composition with a first distance therebetween, and the second marker is longitudinally spaced from the indicator chemical composition with a second distance therebetween. In such an embodiment, the second distance is greater than the first distance. The first pass zone is defined by the location of the first marker and an area beyond the first marker, and the second pass zone is defined by the second marker and an area beyond the second marker.

In an embodiment, the first predetermined temperature is 121° C. and the first predetermined time may be selected from 12 minutes, 15 minutes and 20 minutes. In such an embodiment, the dual indicator can be configured to indicate that an acceptable sterilization level has reached when the indicator chemical composition wicks along the wicking material to a location within in the first pass zone after 12, 15 or 20 minutes of sterilization process at 121° C.

Further, the second predetermined temperature may be 132° C. and the second predetermined period of time may be 4 minutes. In such an embodiment, the dual indicator is configured to indicate that an acceptable sterilization level has reached when the indicator chemical composition wicks along the wicking material to a location within the second pass zone after 4 minutes of sterilization process at 132° C.

In another embodiment, the second predetermined temperature is 134° C. and the second predetermined period of time may be selected from 3.5 minutes, 4 minutes, 5 minutes and 7 minutes. In such an embodiment, the dual indicator is configured to indicate that an acceptable sterilization level has reached when the indicator chemical composition wicks along the wicking material to a location within the second pass zone after 3.5, 4, 5 or 7 minutes of sterilization process at 134° C.

In yet in another embodiment, the second predetermined temperature is 135° C. and the second predetermined period of time is 3 minutes. In such an embodiment, the dual indicator is configured to indicate that an acceptable sterilization level has reached when the indicator chemical composition wicks along the wicking material to a location within the second pass zone after 3 minutes of sterilization process at 135° C.

These and other features and advantages of the present indicator will be apparent from the following detailed description, in conjunction with the appended claims.

BRIEF DESCRIPTION OF THE SEVERAL VIEWS OF THE DRAWINGS

The benefits and advantages of the present device will become more readily apparent to those of ordinary skill in the relevant art after reviewing the following detailed description and accompanying drawings, wherein.

DETAILED DESCRIPTION OF THE INVENTION

Figure 1:
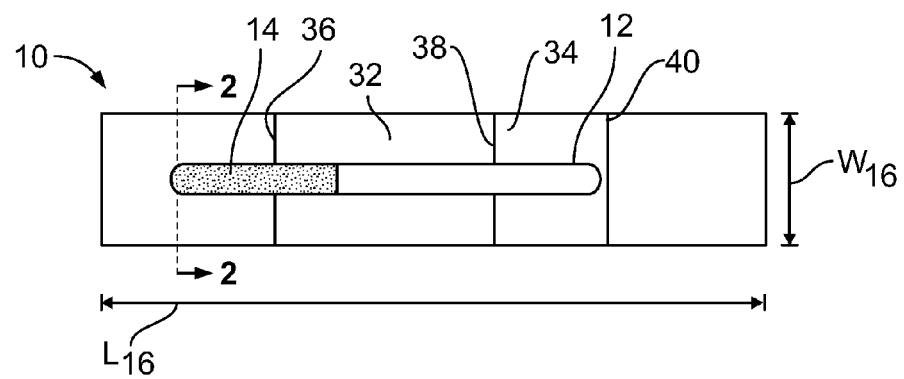
FIG. 1 is a top plan view of a dual indicator according to an embodiment.

While the present device is susceptible of embodiment in various forms, there is shown in the drawings and will hereinafter be described a presently preferred embodiment with the understanding that the present disclosure is to be considered an exemplification of the device and is not intended to be limited to the specific embodiments illustrated.

It should be further understood that the title of this section of this specification, namely, "Detailed Description Of The Invention", relates to a requirement of the United States Patent Office, and does not imply, nor should be inferred to limit the subject matter disclosed herein.

Figure 2:
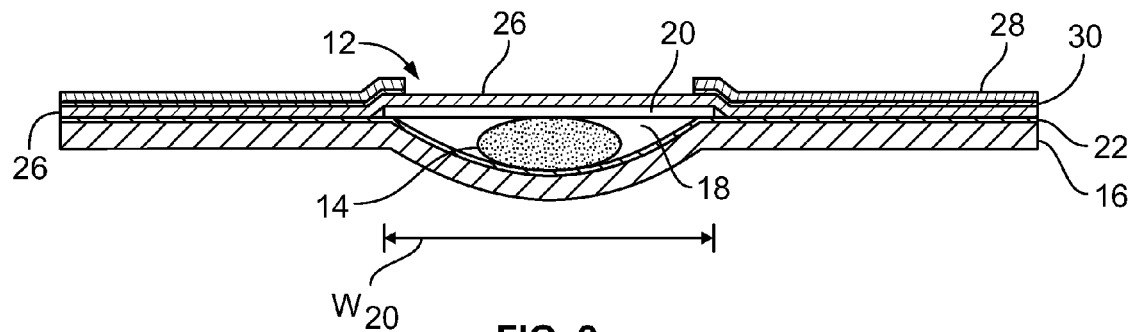
FIG. 2 is a cross-sectional view taken along line 2-2 of FIG. 1.

Referring to FIGS. 1 and 2, an embodiment of a dual indicator 10 is shown. The dual indicator 10 has an open window 12 through which the wicking of an indicator chemical composition 14 can be observed to determine whether an acceptable level of sterilization has occurred as will be described below. As shown, the dual indicator 10 includes two pass zones 32, 34 for indicating whether an acceptable level of sterilization has occurred for two different sterilization conditions. For example, the dual indicator 10 may be configured to work for both 12 minutes at 121° C. sterilization condition and 4 minutes at 134° C. sterilization condition. A first zone 32 is defined by the location of a first marker 36 and the area beyond the first marker 36. A second zone 34 is defined by a second marker 38, and the area beyond the second marker 38.

FIG. 2 is a cross-sectional illustration of the dual indicator 10 of FIG. 1. The dual indicator 10 generally includes a base element 16, a first adhesive layer 22, a wicking element 20, a film layer 26, a second adhesive layer 30, a paper layer 28, and an indicator chemical composition 14. The base element 16 is formed from a foil, for example, an aluminum foil, or other high-heat transfer material. The first adhesive layer 22 is disposed on the base element 16 as a continuous layer covering substantially the entire top surface of the base element 16. The base element has a length $L_{16}$ and width $W_{16}$. A depression 18 is formed in the base element 16 and the first adhesive layer 22. The indicator chemical composition 14 is provided in the recess 18 between the first adhesive layer 22 and the wicking element 20.

Figure 3:
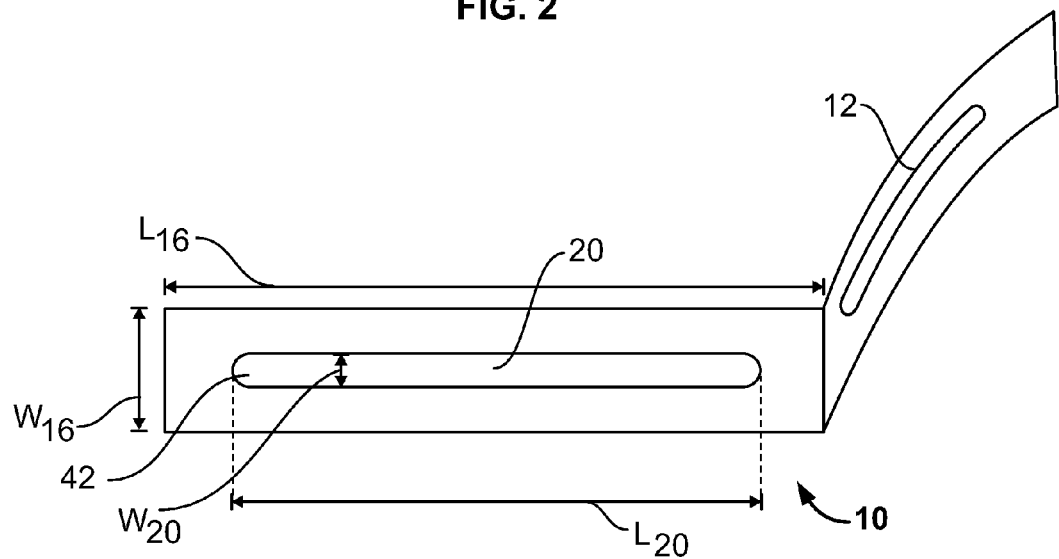
FIG. 3 is a top perspective view of the dual indicator of FIG. 1 with a paper layer, a second adhesive layer, and a film layer peeled off.

The wicking element 20 is disposed on the first adhesive layer 22, and over the indicator chemical composition 14, such that the wicking element 20 is in contact with the indicator chemical composition 14. FIG. 3 is a perspective top view of the dual indicator 10 with the film layer 26, the second adhesive layer 30, and the paper layer 28 peeled away. As shown, the wicking element 20 has a width $W_{20}$ and a length $L_{20}$ that is less than the width $W_{16}$ and the length $L_{16}$ of the base element 16. The wicking element 20 is generally centered on the base element 16 and over the indicator chemical composition 14 in the recess 18, such that an end portion 42 of the wicking element 20 is in contact with the indicator chemical composition 14. The wicking element 20 extends longitudinally along the base element 16, such that at least some portion of the wicking element 20 is securely attached to the base element 20 by the first adhesive layer 22. In this manner, the indicator chemical composition 14 and the wicking element 20 are bounded within the our sides of the dual indicator 10.

A film layer 26 is applied over the base element 16, indicator chemical composition 14, and wicking element 20, and is adhered to the base element. 16 by the first adhesive layer 22. The film layer 26 is a transparent film, as will be discussed in more detail below. The paper layer 28 and the second adhesive layer 30 are disposed over the film layer 26. The paper layer 28 and adhesive layer 30 include the window 12 that is cut out (as seen in FIG. 1) to allow for visual inspection within the window 12, through the film layer 26.

In an embodiment, the base element 16 is formed from an aluminum foil, and a layer of an acrylic adhesive is coated on the base element 16 to form the first adhesive layer 22. In some embodiments, a foil adhesive label having a 3/1000 inch (3 mil) thickness may be used to form the base element 16 and the first adhesive layer 22. Further, an adhesive coated paper may be used to form the paper layer 28 and the second adhesive layer 30. For example, an acrylic adhesive coated paper may be used to form the paper layer 28 and the second adhesive layer 30. The film layer 26 may be formed from a cast polypropylene film having a thickness of about 2.0 to 2.2 mil or 3.0 to 3.2 mil. The wicking element 20 may be formed from a suitable wicking material. For example, the wicking element 20 may be formed from a low-ash, qualitative paper having a basis weight of about 87.7 grams per square meter ($g/m^2$) and a caliper or thickness of about 7.5 thousandths of an inch (mil), or from a white, smooth surface, cotton paper having a basis weight of about 186 $g/m^2$ and a caliper or thickness of about 13.3 mils. The indicator chemical composition 14 may be formed from a temperature sensitive chemical composition. The indicator chemical composition may also contain a colorant in a concentration of about 0.01 percent by weight.

The pass zones 32, 34 are provided on the dual indicator 10, such that the pass zones 32, 34 are visually available to a user. For example, the pass zones 32, 34 may be provided on the paper layer 28. The first pass zone 32 is defined by the location of the first marker 36 and the area beyond the first marker 36. The second pass zone 34 is defined by the second marker 38 and the area beyond the second marker 38. In use, the indicator chemical composition liquefies and wicks along the wicking material 20 when exposed to steam during a sterilization process. At the end of the sterilization process, a user can determine whether an acceptable level of sterilization has occurred by inspecting how far the liquefied indicator chemical composition 14 has moved along the wicking material 20 through the window 12.

For example, after a sterilization process for a last predetermined period of time at a first predetermined temperature (e.g. 12 minutes at 121° C.), a user can determine whether an acceptable level of sterilization has occurred by inspecting whether the indicator chemical composition 14 has reached the first pass zone 32. That is, if the indicator chemical composition 14 has reached the first marker 36 or a location beyond the first marker 36, it indicates that an acceptable level of sterilization has occurred after the sterilization process for the first predetermined period of time at the first predetermined temperature. The user can also use the dual indicator to determine whether an acceptable level of sterilization has occurred after a second predetermined period of time at a second predetermined temperature (e.g. 4 minutes at 134° C.) by inspecting whether the indicator chemical composition 14 has reached the second pass zone 34. That is, if the indicator chemical composition 14 has reached the second marker 38 or a location beyond the second marker 38, it indicates that an acceptable level of sterilization has occurred after the sterilization process for the second predetermined period of time at the second predetermined temperature.

Therefore, the markers 36, 38 are drawn at precalculated distances from the location of the indicator chemical composition 14 according to two different sterilization conditions. As such, the dual indicator 10 can be used to determine whether an acceptable sterilization has occurred after a first predetermined period of time at a first predetermined temperature, or after a second predetermined period of time at a second predetermine temperature. In one embodiment, the dual indicator 10 may be configured to work for a first sterilization condition selected from 12 minutes at 121° C., 15 minutes at 121° C., 20 minutes at 121° C., 30 minutes at 121° C., and a second sterilization condition selected from 4 minutes at 132° C., 3.5 minutes at 134° C., 4 minutes at 134° C., 5 minutes at 134° C., 7 minutes at 134° C., and 3 minutes at 135° C.

In the embodiment shown in FIG. 1, the dual indicator 10 also includes a third line 40. In such an embodiment, the first pass zone 32 may be defined by the area between the first marker 36 and the second marker 38, and the second pass zone may be defined by the second marker 38 and the third line 40. The first pass zone 32 and the second pass zone 34 may be colored in different colors to assist a user in visual inspection of the indicator after a sterilization process. For example, the first pass zone 32 may be colored in a light blue, and the second pass zone 34 may be colored in darker blue, while the rest of the dual indicator 10 surface is in white. In such an embodiment, an acceptable level of sterilization after a sterilization process in a first condition (e.g. 12 minutes at 121° C.) is indicated when the indicator chemical 14 wicks to a location within the first zone 32, as shown in FIG. 1. Although, the indicator chemical 14 may wick beyond the first pass zone 32 and into the second pass zone 34, which also indicates an acceptable sterilization after a sterilization process in the first condition, an acceptable level of sterilization after a sterilization process in the first condition will usually fall within the first pass zone 32. Alternatively, the dual indicator 10 can also be used to indicate an acceptable level of sterilization after a sterilization process in a second condition (e.g. 4 minutes at 134° C.), in which an acceptable level of sterilization is indicated when the indicator chemical 14 wicks to a location within the second pass zone 34.

In one embodiment, the dual indicator 10 is configured such that the indicator chemical composition 14 wicks pass the first marker 36 to reach the first pass zone 32 to indicate that an acceptable level of sterilization has occurred after a first predetermined period of time at a first predetermined temperature, and the indicator chemical composition 14 wicks pass the second marker 38 to indicate that an acceptable level of sterilization has occurred after a second predetermined period of time at a second predetermined temperature. In this preferred embodiment, the dual indicator 10 is configured such that the chemical composition 14 wicks to a location within the first pass zone 32 and does not wick pass the second marker 38 to indicate that an acceptable level of sterilization has occurred after the first predetermined period of time at the first predetermined temperature, even if the dual indicator 10 is left in the sterilization condition longer than the first predetermined temperature. For example, the dual indicator 10 may be configured to indicate an acceptable level of sterilization after 12 minutes at 121° C. or after 4 minutes at 134° C. in which the indicator chemical composition 14 wicks pass the first marker 36 to a location within the first pass zone 32 to indicate that an acceptble level of sterilization has occurred after 12 minutes at 121° C. and does not wick beyond the second marker 38 even if the dual indicator 10 is left in the sterilization condition at 121° C. for more than 12 minutes, for example 30 minutes. Thus, such a dual indicator 10 can reduce a risk of confusion for users since an acceptable level of sterilization for the first sterilization condition is indicated by the indicator chemical composition 14 wicking to a location within the first pass zone 32, but not beyond the second marker 38.

After long research and development, it was discovered that such a dual indicator 10 may be configured by carefully selecting the material and thickness of the film layer 26 in combination of controlling the wicking rate of the indicator chemical composition 14, which may be accomplished by carefully selecting the porosity of the wicking element 20 according to the desired sterilization conditions. In one embodiment, the dual indicator 10 is configured to indicate an acceptable level of sterilization after 12 minutes at 121° C. or after 4 minutes at 134° C., and includes the base element 16, the first adhesive layer 22, the wicking element 20, the film layer 26, the second adhesive layer 30, the paper layer 28, and the indicator chemical composition 14, in which the film layer 26 is formed from a cast polypropylene film having a thickness of about 2.2 mil, and the wicking element 20 is formed from a wicking paper having a basis weight of about 87.7 g/m$^2$ and a thickness of about 7.5 mil. The porosity of the wicking paper correlates with the basis weight and thickness of the wicking paper.

The dual indicator 10 may also be configured to work for different sterilization conditions by adjusting the placement of the first marker 36 and the placement of the second marker 38. For example, the dual indicator 10 may be configured to work for various first and second sterilization condition combinations, in which the first sterilization condition is selected from 12 minutes at 121° C., 15 minutes at 121° C., 20 minutes at 121° C., 30 minutes at 121° C., and the second sterilization condition is selected from 4 minutes at 132° C., 3.5 minutes at 133° C., 4 minutes at 134° C. 5 minutes at 134° C., 7 minutes at 134° C. and 3 minutes at 135° C.

As such, the dual indicator 10 can replace two types of Class 6 sterilization indicators for two different sterilization conditions. The dual indicator 10 meets the performance requirements set for Class 6 indictors set by American National Standards Institute (ANSI)/Association for the Advancement of Medical Instrumentation (AAMI)/International Organization for Standards (ISO) 11140.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be interred. The disclosure is intended to cover all such modifications as fall within the scope of the disclosure.

What is claimed is:

1. An indicator for at least two different sterilization conditions, comprising:
    a base element formed from a thermally conductive material having a length and a width, the base element having a recess formed therein extending along about a longitudinal centerline thereof, the recess formed within the base material less than the length and the width of the base material;
    a first adhesive layer disposed on the base element;
    an indicator chemical composition deposited in the recess;
    a wicking material positioned at least in part in contact with the indicator chemical composition and positioned at least in part within the recess, the wicking material extending less than the length and width of the base element;
    a film layer positioned over the base element, the wicking material and the indicator chemical composition;
    a paper layer disposed over the film layer;
    a second adhesive layer disposed between the paper layer and the film layer, wherein the paper layer and the second adhesive layer include a window therein;
    a first pass zone; and
    a second pass zone;
    wherein, the indicator is configured to indicate that an acceptable level of sterilization has occurred when the indicator chemical composition wicks along the wicking material to a location within the first pass zone after a sterilization process at a first predetermined temperature for a first predetermined period of time, or when the indicator chemical composition wicks along the wicking material to a location within the second pass zone after a sterilization process at a second predetermined temperature for a second predetermined period of time;
    wherein the paper layer includes a first marker and a second marker, wherein the first maker is longitudinally spaced from the indicator chemical composition with a first distance therebetween, and the second marker is longitudinally spaced from the indicator chemical composition with a second distance therebetween, wherein the second distance is greater than the first distance;

wherein the first pass zone is defined by an area between the first marker and the second marker, and the second pass zone is defined by an area beyond the second marker, wherein the indicator is configured to indicate an acceptable level of sterilization after the first predetermined period of time at the first predetermined temperature when the indicator chemical composition wicks to a location within the first pass zone and does not wick beyond the second marker;

wherein the film layer is formed from a cast polypropylene having a thickness of about 2.2 mil, and the wicking material is formed from a wicking paper having a basis weight of about 87.7 g/m$^2$ and a thickness of about 7.5 mil.

2. The indicator of claim 1 wherein the indicator chemical composition contains a temperature sensitive material.

3. The indicator of claim 2 wherein the indicator chemical composition contains a dye.

4. The indicator of claim 1 wherein the base element is aluminum having a thickness of about 3 mils.

5. The indicator of claim 1 wherein the first adhesive layer is formed from an acrylic adhesive.

6. The indicator of claim 1 wherein the second adhesive layer is formed from an acrylic adhesive.

7. The indicator of claim 1, wherein the first sterilization condition is selected from 12 minutes at 121° C., 15 minutes at 121° C., 20 minutes at 121° C., 30 minutes at 121° C., and the second sterilization condition is selected from 4 minutes at 132° C., 3.5 minutes at 134° C., 4 minutes at 134° C., 5 minutes at 134° C., 7 minutes at 134° C., and 3 minutes at 135° C.

* * * * *